(12) United States Patent
Huang

(10) Patent No.: US 8,158,717 B2
(45) Date of Patent: Apr. 17, 2012

(54) ADDITIVE FOR AQUEOUS POLYURETHANE DISPERSION

(75) Inventor: Ching-Tzer Huang, Kaohsiung (TW)

(73) Assignee: Taiwan Hopax Chems. Mfg. Co., Ltd., Kaohsiung (TW)

( * ) Notice: Subject to any disclaimer, the term of this patent is extended or adjusted under 35 U.S.C. 154(b) by 327 days.

(21) Appl. No.: 12/585,326

(22) Filed: Sep. 11, 2009

(65) Prior Publication Data
US 2011/0065849 A1 Mar. 17, 2011

(51) Int. Cl.
*C08G 18/08* (2006.01)
*C08G 18/28* (2006.01)
*C08J 3/00* (2006.01)
*C08K 3/20* (2006.01)
*C08L 75/00* (2006.01)

(52) U.S. Cl. ........ 524/591; 524/589; 524/590; 524/839; 524/840

(58) Field of Classification Search .................. 524/589, 524/590, 591, 839, 840
See application file for complete search history.

(56) References Cited

U.S. PATENT DOCUMENTS
2004/0249012 A1* 12/2004 Tanaka et al. ................... 522/83
* cited by examiner

*Primary Examiner* — Patrick Niland
(74) *Attorney, Agent, or Firm* — Bacon & Thomas, PLLC

(57) ABSTRACT

The present invention relates to glycine derivatives as additive for an aqueous polyurethane dispersion. Said glycine derivatives can increase the fluidity of aqueous polyurethane dispersion and therefore is useful for preparation of aqueous polyurethane dispersion with high solid content. Besides, the glycine derivatives are able to significantly decrease the viscosity of aqueous polyurethane dispersion; therefore, the aqueous polyurethane dispersion with high solid content can be stored stably.

8 Claims, 3 Drawing Sheets

ADDITIVE FOR AQUEOUS POLYURETHANE DISPERSION

BACKGROUND OF THE INVENTION

1. Field of the Invention

The present invention relates to an additive which can increase the fluidity of an aqueous polyurethane dispersion and is useful for preparation of aqueous polyurethane dispersion with high solid content.

2. Description of the Related Art

A polymer of polyurethane (PU) is polymerized by a bi- or multi-functional isocyanate and a polyol. The characters of PU can be changed by varying the chemical structure or ratio of isocyanate and polyol. The structure thereof includes soft segments with low glass transition temperature and hard segments with high polarity, wherein the soft segments are made from polyol with high molecular weight and has the characters of flexibility, rubber-like and non-crystal as well as high extensibility under low stress. Also, the hard segments are crystal, polar and short segments mainly constructed by amino acid ester groups made from the interaction between isocyanate and polyol with low molecular weight and has the characters of non-deformation under extension. The different properties between soft and hard segments result in the microphase separation structure of PU. Moreover, the ratio of isocyanate and polyol can be changed to obtain various properties, such as products with various degree of hardness including elastic body with extreme softness or extreme hardness. Therefore, said PU can be applied to mobile industry, engineering, furniture, wearing, fitness equipment, adhesive agent and etc. Recently, said PU is also used for development and application of biomedical materials and intelligent materials (shape memory polymers).

According to the internal emulsifier used, aqueous polyurethane can be distinguished into non-ionic or ionic type. Ionic aqueous polyurethane can be further distinguished into anionic or cationic type. Common internal emulsifier includes non-ionic coupling agent such as 1,4-butanediol (1,4-BD), cationic internal emulsifier such as methyldiethanolamine (MDEA) and anionic internal emulsifier such as dimethylol propionic acid (DMPA) and 2,2-bis(hydroxymethyl)butyric acid (DMBA).

According to the dispersion character resulted from different solvents used in an polyurethane, polyurethane can be distinguished into aqueous or organic solvent type. Since the aqueous polyurethane has the advantage of good environmental concern and low-cost resulting from reducing the use of organic solvent, it becomes the most of current applications. Common preparation of aqueous polyurethane includes acetone process, prepolymer mixing process, melting dispersion process and etc. The aqueous polyurethane prepared is in the form of emulsion, and the solid content thereof can be adjusted according to its application. Unfortunately, increasing solid content could result in decreasing in fluidity of an aqueous polyurethane dispersion. Therefore, it is an important task for the art to increase the solid content of an aqueous polyurethane dispersion without decreasing the fluidity thereof.

SUMMARY OF THE INVENTION

In view of the disadvantages of conventional technology, one object of the present invention is to provide an additive for an aqueous polyurethane dispersion. The additive has abilities to reduce the viscosity of the aqueous polyurethane dispersion, thereby prolonging the curing time of the aqueous polyurethane dispersion.

Besides, another object of the present invention is to provide an aqueous polyurethane dispersion having good fluidity. The dispersion is able to be enhanced solid content thereof without loss of fluidity.

To achieve the above objects, the present invention provides an additive for an aqueous polyurethane dispersion, having the formula (I):

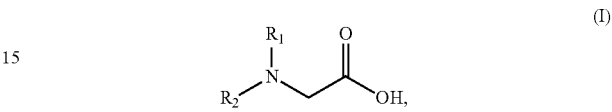

wherein $R_1$ and $R_2$ are independently hydrogen or $-CH_{3-n}(CH_2OH)_n$, provided that $R_1$ and $R_2$ are not hydrogen at the same time; n is 1, 2, or 3.

The present invention also provides an aqueous polyurethane dispersion, comprising an aqueous polyurethane prepolymer; water; and an additive having the formula (I):

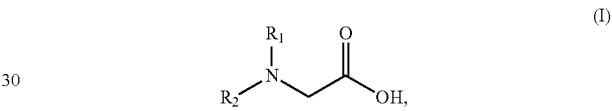

wherein $R_1$ and $R_2$ are independently hydrogen or $-CH_{3-n}(CH_2OH)_n$, provided that $R_1$ and $R_2$ are not hydrogen at the same time; n is 1, 2, or 3.

Yet the present invention provides a use of a compound having the formula (I) as an additive for adjusting the fluidity of an aqueous polyurethane dispersion:

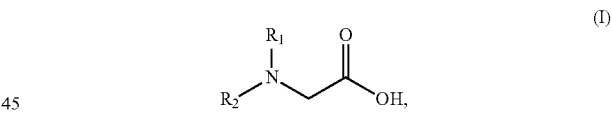

wherein $R_1$ and $R_2$ are independently hydrogen or $-CH_{3-n}(CH_2OH)_n$, provided that $R_1$ and $R_2$ are not hydrogen at the same time; n is 1, 2, or 3.

DETAILED DESCRIPTION OF THE PREFERRED EMBODIMENTS

Figure 1:
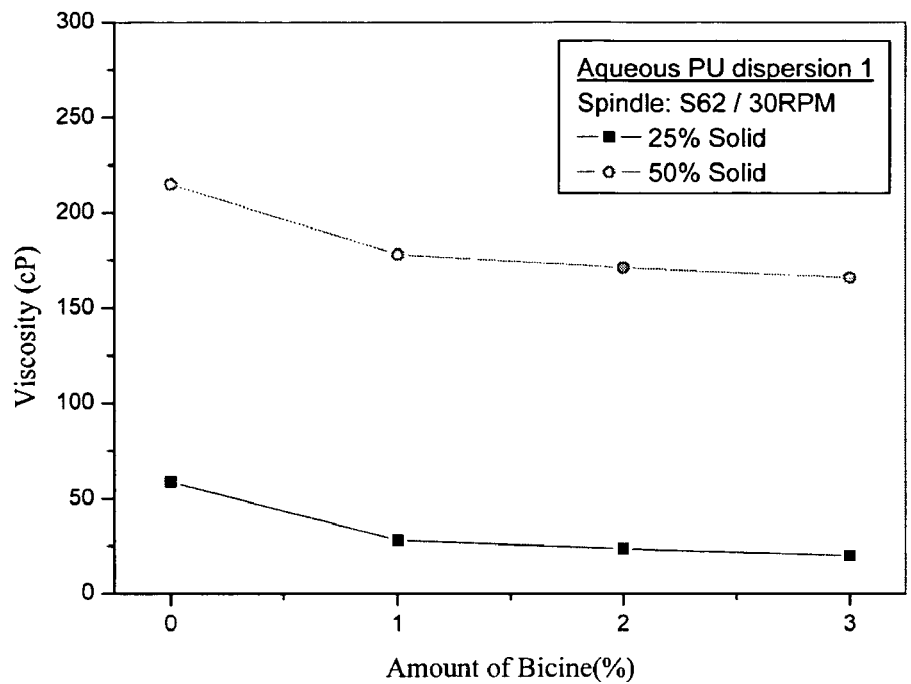
FIG. 1 is a change chart that shows the viscosity of aqueous polyurethane dispersion 1 having bicine in different amounts.

The present invention provides an additive for an aqueous polyurethane dispersion, having the formula (I):

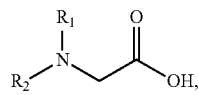
(I)

wherein $R_1$ and $R_2$ are independently hydrogen or $-CH_{3-n}(CH_2OH)_n$, provided that $R_1$ and $R_2$ are not hydrogen at the same time; n is 1, 2, or 3. Preferably, said additive having the formula (I) is N,N-bis(2-hydroxyethyl)glycine or N-[tris(hydroxymethyl)methyl]glycine.

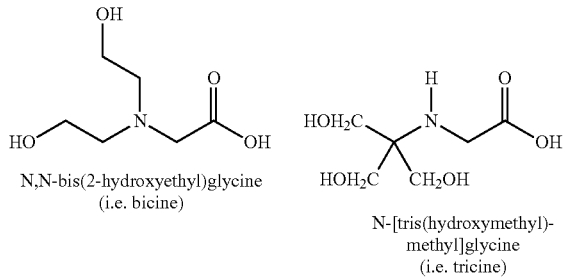

N,N-bis(2-hydroxyethyl)glycine (i.e. bicine)

N-[tris(hydroxymethyl)-methyl]glycine (i.e. tricine)

The present invention also provides an aqueous polyurethane dispersion, comprising an aqueous polyurethane prepolymer; water; and an additive having the formula (I):

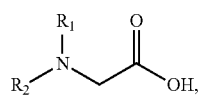
(I)

wherein $R_1$ and $R_2$ are independently hydrogen or $-CH_{3-n}(CH_2OH)_n$, provided that $R_1$ and $R_2$ are not hydrogen at the same time; n is 1, 2, or 3. In a preferred embodiment, said additive having the formula (I) is N,N-bis(2-hydroxyethyl)glycine or N-[tris(hydroxymethyl)methyl]glycine.

The aqueous polyurethane recited in the present invention is made from polymerization of isocyanate with bi- or multi-functional groups, polyol and internal emulsifier. Also, said aqueous polyurethane can be dispersed by aqueous solvent.

The internal emulsifier used for preparation of the aqueous polyurethane of present invention is an ionic internal emulsifier, which is appreciated by those skilled in the art, includes but not limited to cationic methyldiethanolamine (MDEA), anionic dimethylol propionic acid (DMPA) and 2,2-bis(hydroxymethyl)butyric acid (DMBA).

It can be easily understood that the aqueous polyurethane dispersion recited in the present invention comprises water as solvent and water-soluble polyurethane prepolymer. The ratio between said water and said water-soluble polyurethane prepolymer can be adjusted as requested. Whereas, the amount of the additive is 0.1~5 wt % of the total weight of said dispersion. Preferably, the amount of the additive is 0.5~3 wt %.

Moreover, the present invention provides a use of a compound having the formula (I) as an additive for adjusting the fluidity of an aqueous polyurethane dispersion:

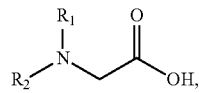
(I)

wherein $R_1$ and $R_2$ are independently hydrogen or $-CH_{3-n}(CH_2OH)_n$, provided that $R_1$ and $R_2$ are not hydrogen at the same time; n is 1, 2, or 3. In a preferred embodiment, said compound having the formula (I) is N,N-bis(2-hydroxyethyl)glycine or N-[tris(hydroxymethyl)methyl]glycine.

In the use recited in the present invention, the amount of said compound having the formula (I) is 0.1-5 wt % of the total weight of the aqueous polyurethane dispersion. Preferably, the amount of said compound having the formula (I) is 0.5-3 wt %.

The examples of this invention are provided hereinafter, however, these examples are not used for limit the present invention. Any amendments and modifications can be made by those skilled in the art without departing the spirit and scope of the present invention. The scope of the present invention is defined by the appended claims.

EXAMPLE 1

Preparation of Aqueous Polyurethane Dispersion 1

100 g of commercial aqueous polyurethane prepolymer (poly(propyleneglycol)/DMPA/IPDI(isophorone diisocyanate)/acetone; the ratio of components thereof is 49.5/2.5/18/30) was diluted with appropriate acetone and stirred by machine in a 250 mL beaker. Then, one drop of Triethylamine (TEA) was added into the beaker as neutralizer. After being stirred continually for 10 minutes, the well-mixed solution was dropped slowly into water, which was stirred at high speed (the amount of the water can be adjusted as requested). After dropping all the solution, the aqueous polyurethane prepolymer was dispersed uniformly into the water by continually stirring at high speed for 20 minutes. Then, acetone was withdrawn by using decompression concentrator to obtain aqueous polyurethane dispersion 1 with various solid contents.

EXAMPLE 2

Preparation of Aqueous Polyurethane Dispersion 2

248.2 g of IPDI was slowly dropped into a mixture of 600 g of polytetramethylene ether glycol (PTMEG-1000) and 35 g of DMPA in a four-necked bottle equipped with a condensation tube. The resulting mixture was heated to 100° C. by heating mantle and was stirred for 3 hours by machine. After being cooled to 60° C., the mixture was diluted with 500 mL of acetone and then cooled to room temperature to obtain PTMEG/DMPA/IPDI/acetone type of aqueous polyurethane prepolymer. 100 g of said aqueous polyurethane prepolymer was put into a 250 mL beaker and stirred by machine. One drop of Triethylamine (TEA) was added inside as neutralizer. After continually stirring for 10 minutes, the well-mixed solution was dropped slowly into water, which was stirred at high speed (the amount of the water can be adjusted as requested). After dropping all the solution, the aqueous polyurethane prepolymer was dispersed uniformly into the water by continually stirring at high speed for 20 minutes. Then, acetone was withdrawn by using decompression concentrator to obtain aqueous polyurethane dispersion 2 with various solid contents.

EXAMPLE 3

Preparation of Aqueous Polyurethane Dispersion 3

143.92 g of IPDI was slowly dropped into a mixture of 600 g of polytetramethylene ether glycol (PTMEG-1000) and 24 g of sulfonated diol (MS-400 of Taiwan HOPAX chemicals MFG. CO. LTD) in a four-necked bottle equipped with a condensation tube. The resulting mixture was heated to 100° C. by heating mantle and was stirred for 3 hours by machine. After being cooled to 60° C., the mixture was diluted with 500 mL of acetone and then cooled to room temperature to obtain PTMEG/sulfonated diol/IPDI/acetone type of aqueous polyurethane prepolymer. 100 g of said aqueous polyurethane prepolymer was put into a 250 mL beaker and stirred by machine. One drop of Triethylamine (TEA) was added inside as neutralizer. After continually stirring for 10 minutes, the well-mixed solution was dropped slowly into water, which was stirred at high speed (the amount of the water can be adjusted as requested). After dropping all the solution, the aqueous polyurethane prepolymer was dispersed uniformly into the water by continually stirring at high speed for 20 minutes. Then, acetone was withdrawn by using decompression concentrator to obtain aqueous polyurethane dispersion 3 with various solid contents.

EXAMPLE 4

Viscosity Test for Aqueous Polyurethane Dispersion 1 Having the Additive of Present Invention Aqueous polyurethane dispersion 1 with 25% or 50% solid content was prepared according to the method set forth in example 1. The additive of present invention was added into said aqueous polyurethane dispersions. Then the viscosity was tested at 30 rpm to examine the viscosity of aqueous polyurethane dispersions having bicine and tricine of different weight percentage by using viscometer with $S_{62}$ spindle. The result was presented as FIGS. 1 and 2, respectively.

Figure 2:
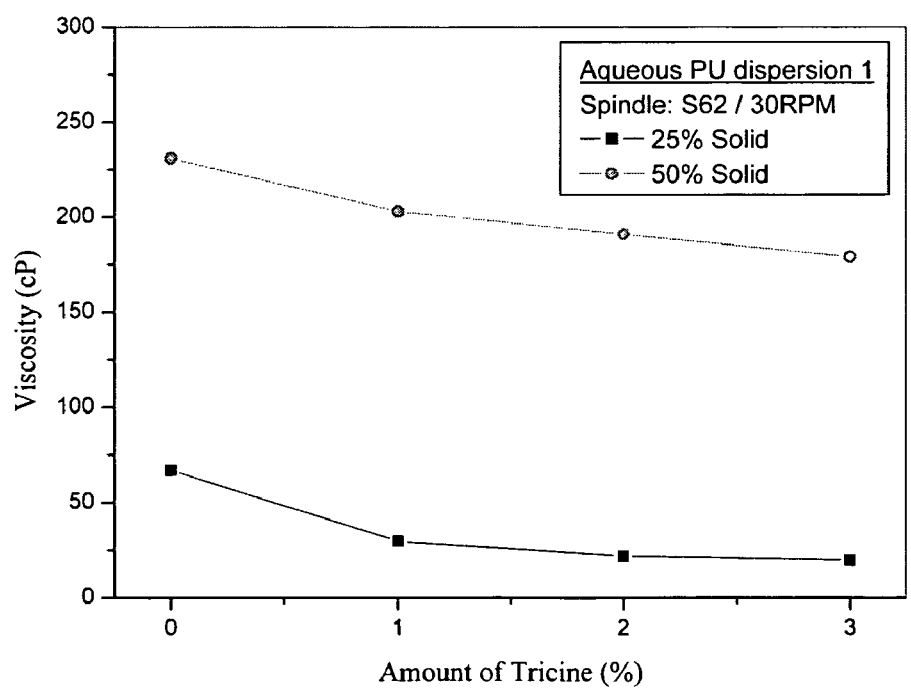
FIG. 2 is a change chart that shows the viscosity of aqueous polyurethane dispersion 1 having tricine in different amounts.

According to FIGS. 1 and 2, the viscosity of the aqueous polyurethane dispersions was decreased significantly by adding 1 or more % of bicine or tricine.

EXAMPLE 5

Viscosity Test for Aqueous Polyurethane Dispersion 2 Having Additive of Present Invention Aqueous polyurethane dispersion 2 with 40%, 50% or 60% solid content was prepared according to the method set forth in example 2. The additive of present invention was added into said aqueous polyurethane dispersions. Then the viscosity was tested at 30 rpm to examine the viscosity of aqueous polyurethane dispersions having bicine and tricine of different weight percentage by using viscometer with $S_{63}$ spindle. The result was presented as FIGS. 3 and 4, respectively.

Figure 3:
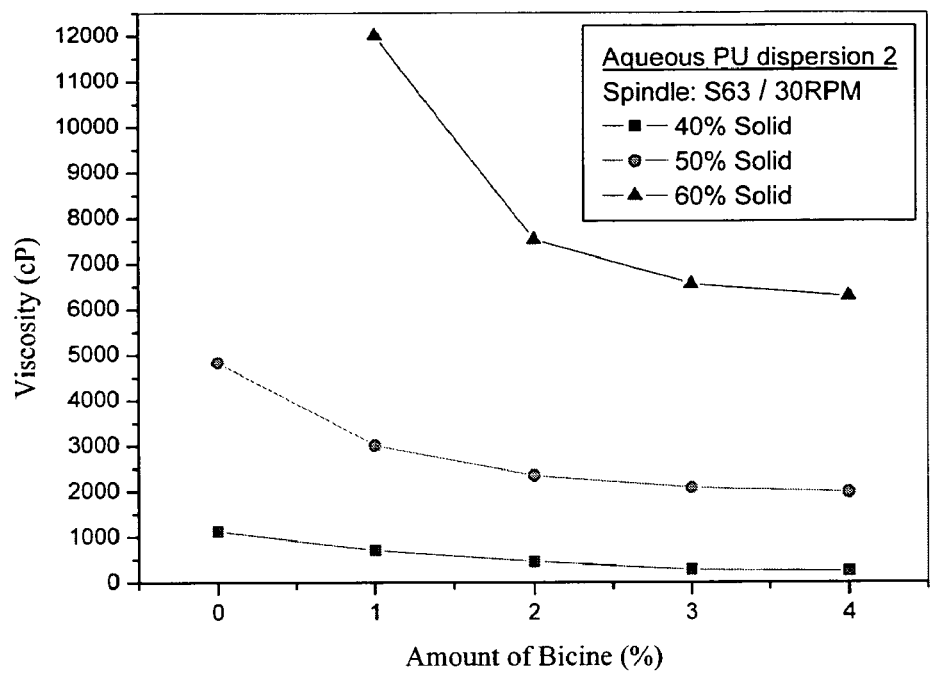
FIG. 3 is a change chart that shows the viscosity of aqueous polyurethane dispersion 2 having bicine in different amounts.
Figure 4:
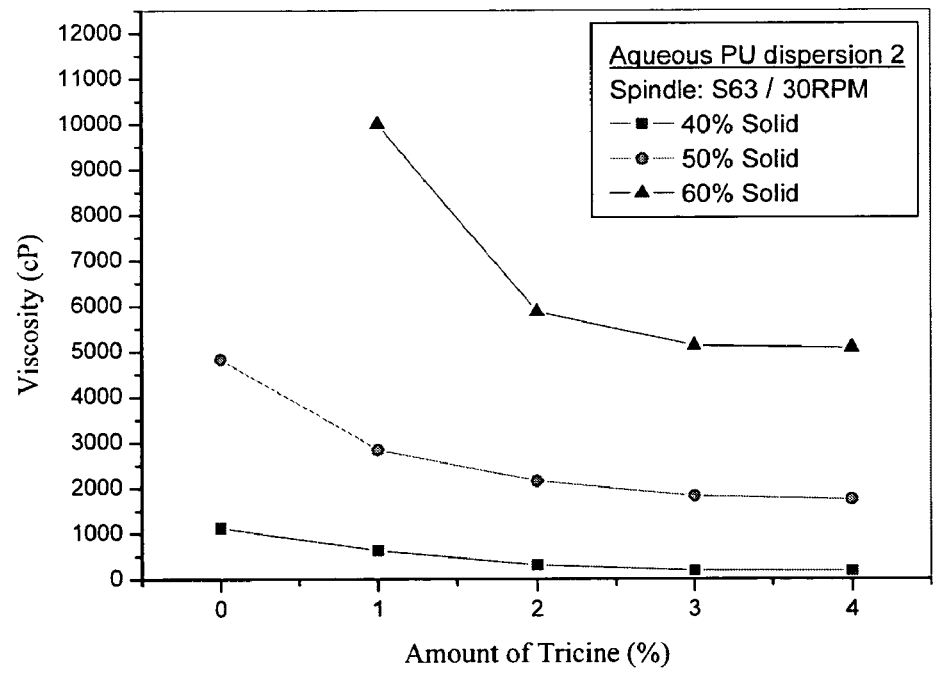
FIG. 4 is a change chart that shows the viscosity of aqueous polyurethane dispersion 2 having tricine in different amounts.

According to FIGS. 3 and 4, the viscosity of the aqueous polyurethane dispersions was decreased significantly by adding 1 or more % of bicine or tricine.

EXAMPLE 6

Viscosity Test for Aqueous Polyurethane Dispersion 3 Having Additive of Present Invention Aqueous polyurethane dispersion 3 with 40%, 50% or 60% solid content was prepared according to the method set forth in example 3. The additive of present invention was added into said aqueous polyurethane dispersions. Then the viscosity was tested at 30 rpm to examine the viscosity of aqueous polyurethane dispersions having bicine and tricine of different weight percentage by using viscometer with $S_{63}$ spindle. The result was presented as FIGS. 5 and 6, respectively.

Figure 5:
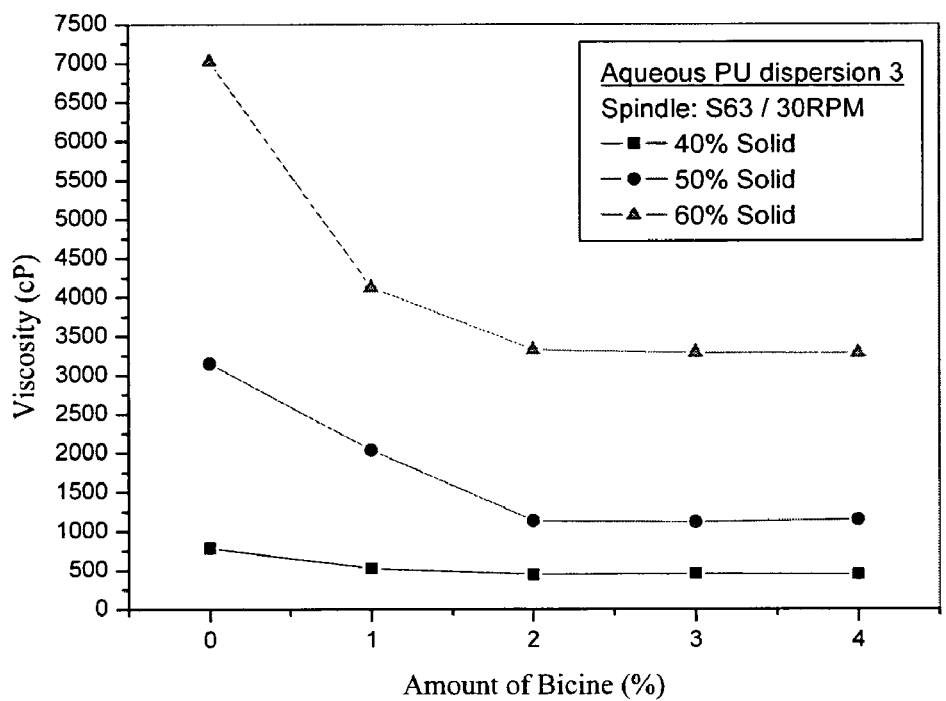
FIG. 5 is a change chart that shows the viscosity of aqueous polyurethane dispersion 3 having bicine in different amounts.
Figure 6:
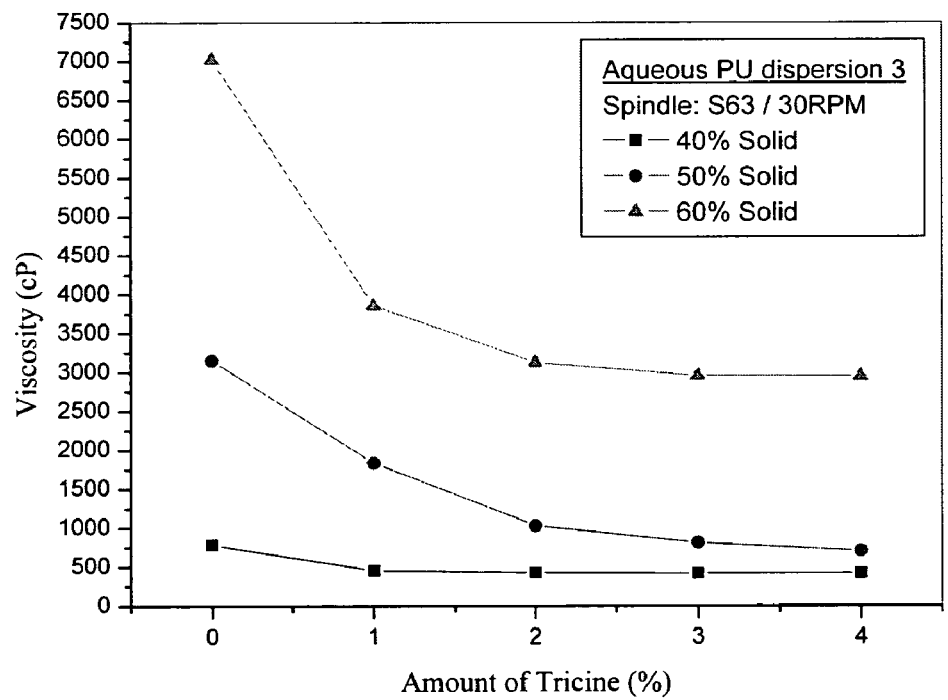
FIG. 6 is a change chart that shows the viscosity of aqueous polyurethane dispersion 3 having tricine in different amounts.

According to FIGS. 5 and 6, the viscosity of the sulfonic acid type aqueous polyurethane dispersions was decreased significantly by adding 1 or more % of bicine or tricine.

EXAMPLE 7

Effect on Curing of Aqueous Polyurethane Dispersion Having Additive of Present Invention For clearly demonstrating the inventive step of present invention, the comparison of curing time between commercial aqueous polyurethane dispersion and the aqueous polyurethane dispersion having additive of present invention was made as shown Table 1.

Aqueous polyurethane prepolymers from example 1 were mixed with the additive of present invention in the amount of 3 wt % to prepare aqueous polyurethane dispersions with 40%, 50% or 60% solid content. Said aqueous polyurethane dispersions were well-mixed and placed steady at room temperature to observe the fluidity and curing thereof. The result was shown in Table 1:

TABLE 1

| aqueous | Solid content | | |
|---|---|---|---|
| PU dispersions | 40% | 50% | 60% |
| without additive | moderate fluidity | cured after 5 days | cured after 10 minutes |
| 3% bicine added | high fluidity | moderate fluidity | cured after 10 days |
| 3% tricine added | high fluidity | moderate fluidity | high viscosity solution |

According to above information, the additive of present invention has the ability to prolong the curing time of an aqueous polyurethane dispersion, and therefore is useful to make an aqueous polyurethane dispersion with high solid content. The result showed that the additive of present invention has the ability to increase the fluidity of an aqueous polyurethane dispersion with high solid content.

To sum up, the present invention discloses glycine derivatives as additive can increase the fluidity of aqueous polyurethane dispersion, and therefore are useful for preparation of aqueous polyurethane dispersion with high solid content.

OTHER EXAMPLES

The preferred embodiments of the present invention have been disclosed in the examples. All modifications and alterations without departing from the spirits of the invention and appended claims, including the other embodiments shall remain within the protected scope and claims of the invention.

The preferred embodiments of the present invention have been disclosed in the examples. However the examples should not be construed as a limitation on the actual applicable scope of the invention, and as such, all modifications and alterations without departing from the spirits of the invention and appended claims, including the other embodiments shall remain within the protected scope and claims of the invention.

What is claimed is:

1. An aqueous polyurethane dispersion, comprising:
an aqueous polyurethane prepolymer;
water; and
an additive having the following formula (I):

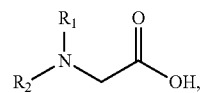

wherein $R_1$ and $R_2$ are each independently hydrogen or $-CH_{3-n}(CH_2OH)_n$; $R_1$ and $R_2$ are not both hydrogen; and n is 2 or 3.

2. The aqueous polyurethane dispersion of claim 1, wherein said additive is N-[tris(hydroxymethyl)methyl]glycine.

3. The aqueous polyurethane dispersion of claim 1, wherein said additive is present in the amount of 0.1-5 wt %.

4. The aqueous polyurethane dispersion of claim 3, wherein said additive is present in the amount of 0.5-3 wt %.

5. A method for increasing the fluidity of an aqueous polyurethane dispersion, wherein said method comprises adding a compound having the following formula (I) as an additive to said aqueous polyurethane dispersion:

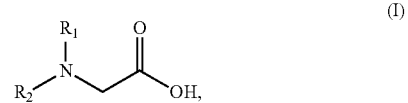

wherein $R_1$ and $R_2$ are each independently hydrogen or $-CH_{3-n}(CH_2OH)_n$; $R_1$ and $R_2$ are not both hydrogen; and n is 2 or 3; and wherein said compound increases the fluidity of said aqueous polyurethane dispersion.

6. The method of claim 5, wherein said compound is N-[tris(hydroxymethyl)methyl]glycine.

7. The method of claim 5, wherein said compound is added to a concentration of 0.1-5 wt %.

8. The method of claim 7, wherein said compound is added to a concentration of 0.5-3 wt %.

* * * * *